US009090863B2

(12) United States Patent
Breuer et al.

(10) Patent No.: US 9,090,863 B2
(45) Date of Patent: Jul. 28, 2015

(54) SYSTEM FOR SEEDING CELLS ONTO THREE DIMENSIONAL SCAFFOLDS

(75) Inventors: Christopher Breuer, Bethany, CT (US); Edward L. Snyder, Wallingford, CT (US); Keru O. Shafi, Anaheim Hills, CA (US); Martin A. Smith, Northport, NY (US)

(73) Assignees: PALL CORPORATION, Port Washington, NY (US); YALE UNIVERSITY, New Haven, CT (US)

( * ) Notice: Subject to any disclaimer, the term of this patent is extended or adjusted under 35 U.S.C. 154(b) by 0 days.

(21) Appl. No.: 12/781,367

(22) Filed: May 17, 2010

(65) Prior Publication Data
US 2011/0281358 A1 Nov. 17, 2011

(51) Int. Cl.
C12N 5/00 (2006.01)
C12M 3/00 (2006.01)
C12M 1/12 (2006.01)
C12M 1/00 (2006.01)

(52) U.S. Cl.
CPC .............. *C12M 21/08* (2013.01); *C12M 25/14* (2013.01); *C12M 29/04* (2013.01)

(58) Field of Classification Search
CPC ....... C12M 21/08; C12M 29/04; C12M 29/12
USPC .................. 435/289.1, 395; 600/36
See application file for complete search history.

(56) References Cited

U.S. PATENT DOCUMENTS

| | | | |
|---|---|---|---|
| 5,266,480 A | 11/1993 | Naughton et al. | |
| 5,451,321 A | 9/1995 | Matkovich | |
| 5,501,971 A | 3/1996 | Freedman et al. | |
| 5,792,603 A * | 8/1998 | Dunkelman et al. | 435/1.2 |
| 5,998,184 A | 12/1999 | Shi | |
| 6,218,182 B1 * | 4/2001 | Naughton et al. | 435/395 |
| 6,416,995 B1 | 7/2002 | Wolfinbarger | |
| 7,291,450 B2 * | 11/2007 | Sowemimo-Coker et al. | 435/2 |
| 2003/0093034 A1 | 5/2003 | Chang et al. | |
| 2004/0039441 A1 | 2/2004 | Rowland et al. | |
| 2005/0008626 A1 | 1/2005 | Fraser et al. | |
| 2005/0048644 A1 * | 3/2005 | Hedrick et al. | 435/289.1 |
| 2005/0205498 A1 | 9/2005 | Sowemimo-Coker et al. | |
| 2005/0214344 A1 | 9/2005 | Barrows et al. | |
| 2007/0224677 A1 | 9/2007 | Neumann | |

FOREIGN PATENT DOCUMENTS

| | | |
|---|---|---|
| JP | H08-506019 A | 7/1996 |
| JP | H11-504216 A | 4/1999 |
| JP | 2001-000178 A | 1/2001 |
| JP | 2002-291867 A | 10/2002 |
| JP | 2002-534210 A | 10/2002 |
| JP | 2004-508305 A | 3/2004 |
| JP | 2007-530575 A | 11/2007 |
| JP | 2009-531067 A | 9/2009 |
| JP | 2009-540878 A | 11/2009 |
| KR | 1999-0008070 A | 10/2000 |
| KR | 2001-0024824 A | 3/2001 |
| KR | 2005-006147 A | 1/2005 |
| KR | 2009-0042529 A | 4/2009 |
| WO | WO 91/17809 | 11/1991 |
| WO | WO 96/34090 A1 | 10/1996 |
| WO | WO 00/41648 A1 | 7/2000 |
| WO | WO 02/18441 A2 | 3/2002 |
| WO | WO 2007/146261 A2 | 12/2007 |
| WO | WO 2009/054609 A1 | 4/2009 |

OTHER PUBLICATIONS

PCT International Search Report and Written Opinion dated Aug. 4, 2010.
International Preliminary Report on Patentability; International Application No. PCT/US2010/35109, dated Nov. 20, 2012.
Notice of Reasons for Rejection, JP Application No. P2013-511133 dated Feb. 25, 2014.
Notice of Allowance of Patent, Korean Application No. 10-2012-7030134 dated May 27, 2014.

* cited by examiner

*Primary Examiner* — Jim Ketter
*Assistant Examiner* — Antonio Galisteo Gonzalez
(74) *Attorney, Agent, or Firm* — Leydig, Voit & Mayer

(57) ABSTRACT

Systems are provided for convenient and sterile isolation, collection, and seeding of cells onto a scaffold or tissue graft. The systems may be closed. Methods for use of the disclosed systems for isolation, collection and seeding of cells and generation of tissue engineered vascular grafts are also provided. The systems may be supplied in kits for efficient and expeditious use.

34 Claims, 4 Drawing Sheets

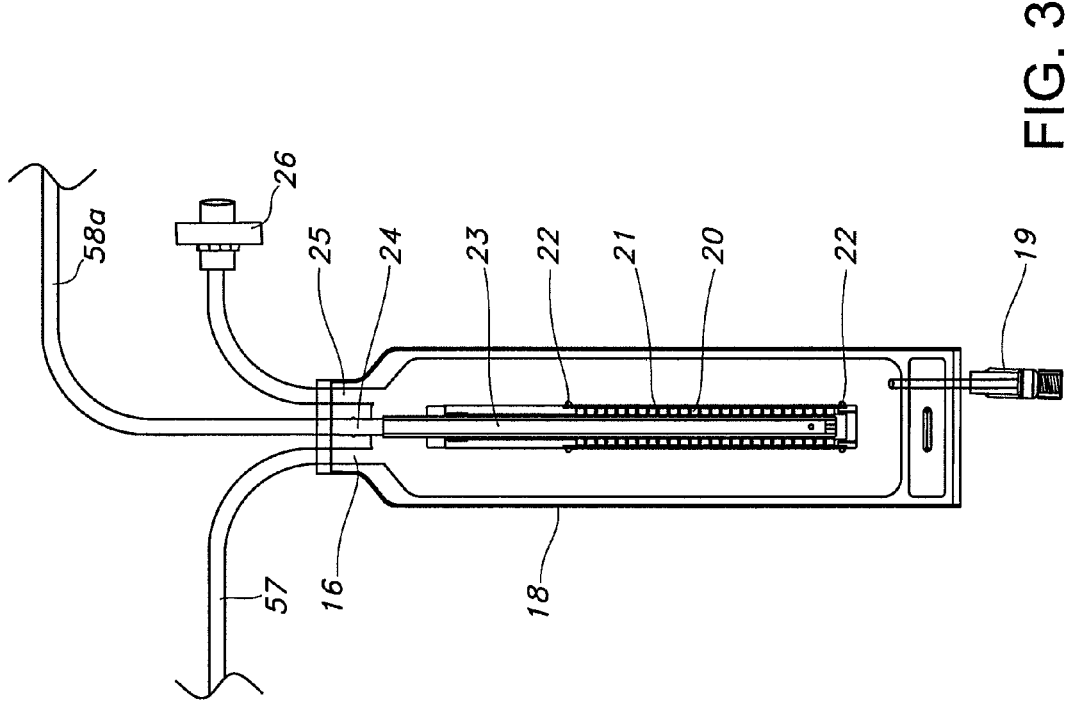

SYSTEM FOR SEEDING CELLS ONTO THREE DIMENSIONAL SCAFFOLDS

STATEMENT REGARDING GOVERNMENT SPONSORED RESEARCH

The U.S. Government has certain rights in this invention pursuant to the following grants: 5K08HL083980-05 awarded to Dr. Christopher Breuer by the United States National Institutes of Health (NIH).

FIELD OF THE INVENTION

The present invention relates to a system, including an apparatus and method for the collection, isolation, seeding of cells from a source, e.g., an individual, directly onto a biocompatible scaffold in preparation for implantation.

BACKGROUND INFORMATION

Vascular and cardiothoracic surgeons use vascular grafts to repair or replace segments of arterial and venous blood vessels that are weakened, damaged, or obstructed due to trauma or disease such as aneurysm, atherosclerosis, and infection. Historically, vascular grafts have been either homografts, such as the patient's own saphenous vein or internal mammary artery, prosthetic grafts made of synthetic materials such as polyester (e.g., Dacron), expanded polytetrafluoroethylene (ePTFE), and other composite materials, or fresh or fixed biological tissue grafts.

However, synthetic grafts generally have inadequate patency rates for many uses, while the harvesting of homografts requires extensive surgery which is time-consuming, costly, and traumatic to the patient. Fixed tissue grafts do not allow for infiltration and colonization by the host cells, which is essential to remodeling and tissue maintenance. Consequently, fixed tissue grafts degrade with time and will eventually malfunction.

Due to the inadequacies of these currently available synthetic and biological grafts, and the high cost and limited supply of homografts, tissue engineered grafts are being developed which are sterilized, then seeded and cultured, in vitro, with cells. These tissue engineered grafts may be superior to other grafts for use in replacement therapy in that they may display the long term dimensional stability and patency of native arteries and vessels with normal physiologic functionality.

Historically, cell isolation and seeding in addition to culturing of tissue-engineered grafts generally requires the use of a sterile environment, such as a hood or specialized facility, such as an ISO Class 7 room. However, there are disadvantages to seeding and culturing tissue in such an environment. For example, these systems can be cumbersome for the user, inconvenient, time-consuming to use, and very expensive to build and maintain.

Thus, there exists a need in the art for compositions and methods that allow for the convenient, sterile isolation, collection and seeding of tissue engineered grafts and other prosthetic devices.

SUMMARY

Described herein is a system, preferably, a closed, sterile system, including an apparatus and methods, for isolating and collecting cells, e.g., bone marrow-derived progenitor cells, such as mononuclear cells, from a source, preferably, a subject, and then seeding them onto a biocompatible, three-dimensional scaffold or tissue graft. The scaffold or graft can be further incubated within the system for culture, transport, storage, testing and/or implantation into a subject, e.g., as a tissue graft, such as a vascular graft, to regenerate and/or repair a tissue in vivo, in vitro or ex vivo.

In accordance with the present invention, there is provided an apparatus and method for isolating and seeding, culturing, storing, shipping, and testing vascular grafts within a closed and sterile system that does not requires a specialized hood or clean room. In certain aspects, the present invention provides an apparatus and method for seeding and culturing vascular grafts with human cells, resulting in a tissue engineered vascular graft populated with viable human cells.

In certain aspects, the invention provides a closed, disposable system that isolates the desired cell type using a filtration/elution technique, and seeds the cells onto a three-dimensional biocompatible scaffold using vacuum seeding. The seeded scaffold can then be incubated and removed from the system when ready for use.

Accordingly, in one aspect, a system for seeding cells is provided comprising a cellular isolate fluid container; a flow channel disposed between the cellular isolate fluid container and a collection fluid container, an elution fluid container, and a seeding container, wherein the flow channel comprises an inlet, an outlet and a filter therebetween, wherein the filter is adapted to allow flow in at least two directions, and wherein the flow channel is selectively in fluid communication with each of the cellular isolate fluid container; the collection fluid container, the elution fluid container, and the seeding container, respectively. In certain embodiments, the seeding container comprises a porous or perforated tube, e.g., a perforated mandril, and a biocompatible three-dimensional scaffold which is apposed to at least a portion of the tube. In certain additional embodiments, the system includes a residual seeded cell fluid container in fluid communication with the seeding container, and a vacuum source in fluid communication with the residual seeded cell fluid container.

In another aspect, methods for using a system for seeding cells as described herein is provided.

The present invention further provides any invention described herein.

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which:

FIG. 3 illustrates another seeding container (18) that can be used in accordance with embodiments of the invention.

DETAILED DESCRIPTION

Figure 1:
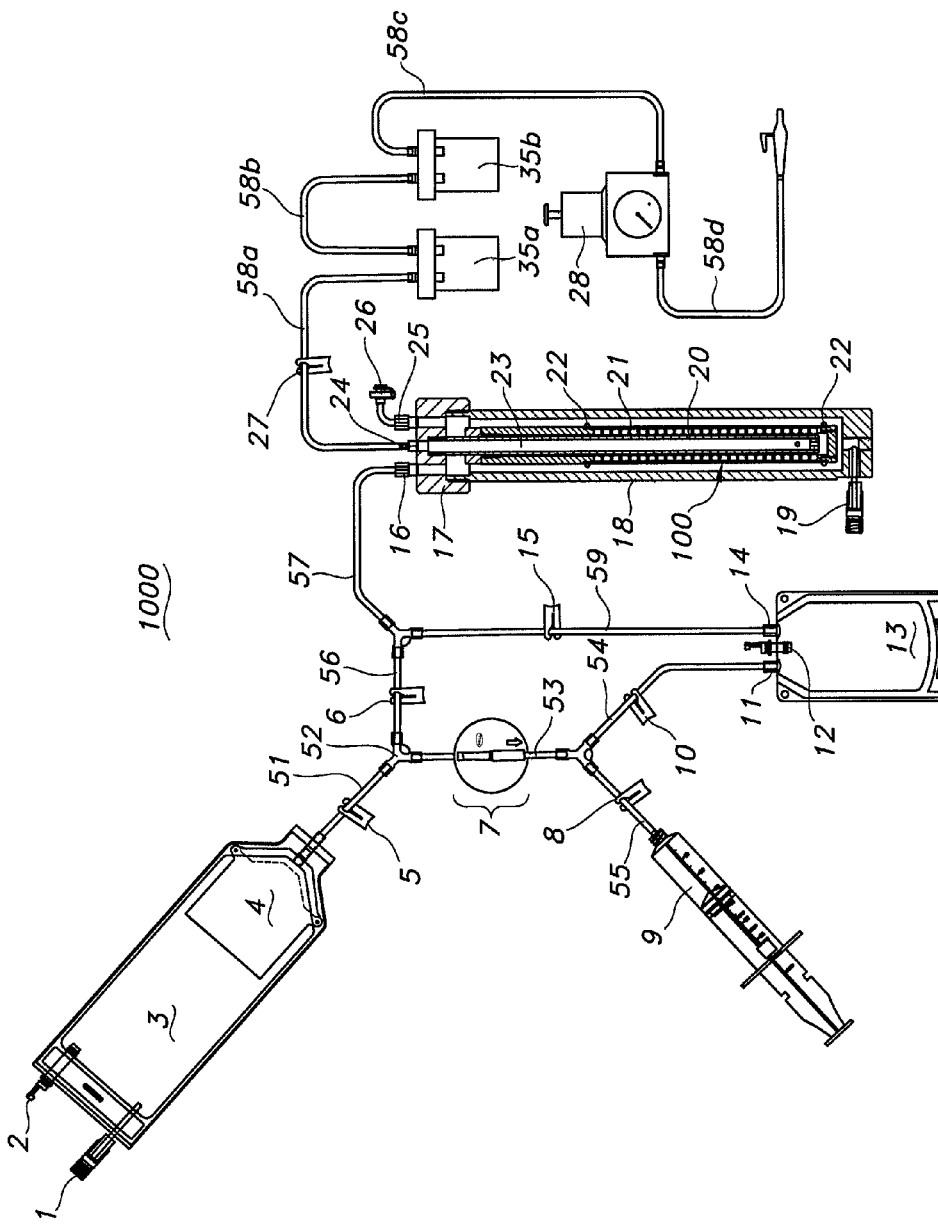
FIG. 1 demonstrates an exemplary system as described herein. Briefly, (i) a bone marrow aspirate (e.g., 5 cc/kg body weight) is aseptically collected and injected into cell isolate fluid container (3); (ii) using gravity, the bone marrow aspirate is passed through a flow channel (7) including a filter which traps the bone marrow derived-mononuclear cells as the aspirate passes from the upstream surface of the filter medium and through the downstream surface of the filter medium; (iii) the remaining portion of the bone marrow aspirate (which is typically composed primarily of plasma, but may include red blood cells and/or platelets) is collected in collection fluid container (13); (iv) the elution solution in elution fluid container (9) is passed through the flow channel (7), wherein the elution solution passes from the downstream surface of the filter medium and through the upstream surface of the medium, and into a seeding container (18) such that the filter releases the bone marrow-derived mononuclear cells which are collected in the seeding container; (v) the seeding container (18) contains a scaffold that is inserted over a perforated mandril (20); (vi) the bone marrow-derived mononuclear cell suspension fills the seeding container (18) completely covering the scaffold that is inserted over the perforated mandril (20); (vii) a vacuum (e.g., −20 mm Hg) is applied until all of the cell suspension has passed through the scaffold and is collected in at least one residual seeded cell fluid container (35a, 35b); and (viii) the filtered bone marrow aspirate, typically primarily comprising plasma, is passed, via gravity, from the collection container (13), into seeding container (18), which contains the seeded scaffold, thus bathing the seeded scaffold.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Described herein is a system, preferably, a closed, sterile system, including an apparatus and methods, for isolating and collecting cells, e.g., bone marrow-derived progenitor cells, such as mononuclear cells, which are seeded onto a biocompatible, three-dimensional scaffold, incubated, and which can then be, for example, implanted, e.g., as a tissue graft, such as a vascular graft. In certain embodiments, the system utilizes a filtration/elution technique, for sterile isolation, seeding, and incubation of cells on to three-dimensional scaffolds. The sterile isolated cells populating the biocompatible scaffold can be cultured and employed in storing, shipping, and/or testing the cells from an individual. Alternatively, the scaffold populated with viable isolated cells can be cultured and used, for example, as an implantable graft, e.g., a vascular graft, to regenerate and/or repair a tissue in vivo, in vitro or ex vivo.

Thus, one advantage of the present invention is that it provides a convenient, relatively low-cost system for sterilely isolating, seeding, and incubating cells onto a scaffold without the need for a hood or specialized facility such as an ISO Class 7 room. Another advantage is that the method can be carried out quicker than conventional methods using a hood or specialized facility. Advantageously, for example, the method can be carried out in a few hours, e.g., about 5 hours or less, preferably, about 3 hours or less, even more preferably, about two (2) hours or less.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

I. Exemplary Definitions

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991). As used herein, the following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

In order that the present invention may be more readily understood, certain terms are first defined.

The term "mandril" can mean, but in no way limited to, a cylindrical device or tube, e.g., a metal bar, that serves as a core around which material, e.g., a matrix scaffold for seeding and growing cells, may be cast, molded, forged, bent, or otherwise shaped. In certain embodiments, the mandril described herein is open on at least one end. In additional embodiments, the mandril described herein may also contain holes or perforations along its axis (i.e., along its length).

The term "valve" can mean, but in no way limited to, a device or part of a device by which the flow of liquid, gas, or loose material may be started, stopped, or regulated, e.g., by a movable part that opens, shuts or partially obstructs one or more ports (e.g., inlet or outlet) or passageways.

The term "biocompatible" can mean, but is not limited to, a material that the body generally accepts without a major immune response, which is capable of implantation in biological systems, for example, tissue implantation, without causing excessive fibrosis or rejection reactions.

The term "biodegradable" can mean, but is not limited to, the ability of a substance or material to break down into harmless substances by the action of a living organism(s).

The term "polymer" can mean, but is not limited to, a macromolecule formed by the chemical union of five or more identical combining units called monomers. In most cases, the number of monomer is quite large and often is not precisely known. In synthetic polymers, this number may be controlled to a predetermined extent. Combinations two, three, or four monomers are called, respectively, dimers, trimers, and tetramers, and are known collectively as oligomers. Polymers may be inorganic (e.g., siloxane, sulfur chains, black phosphorus, boron-nitrogen, silicones) or organic (meaning containing carbon). Organic polymers may be natural (e.g., polysaccharides, such as starch, cellulose, pectin, seaweed gums, vegetable gums; polypeptides, such as casein, albumin, globulin, keratin, insulin, DNA; and hydrocarbons], synthetic (such as, for example, thermoplastics (e.g., unvulcanized elastomers, nylon, polyvinyl chloride, linear polyethylene, polystyrene, polypropylene, polyurethane, acrylate resins); thermosetting (e.g., vulcanized elastomers, crosslinked polyethylene, phenolics, alkyds, polyesters), and semisynthetic (e.g., cellulosics, such as rayon, methylcellulose, cellulose acetate; and modified starches)].

The term "homopolymer" can mean, but is not limited to, a natural or synthetic polymer derived from a single monomer.

The term "heteropolymer" can mean, but is not limited to, a natural or synthetic polymer derived from more than one monomer subunit (i.e., co-polymer). Unless otherwise indicated, the term "polymer" is used generally to refer to both homopolymers and heteropolymers (i.e., co-polymer) as described herein.

The term "water soluble cellulose compounds" can mean, but is not limited to, a family of cellulose compounds that are long chain macromolecules of repeating glucose units substituted to varying extents with anionic sulfate groups, which can be represented as $—SO_3^-$. Molecular weights of water soluble cellulose compounds encompassed by the invention typically range from about $5 \times 10^5$ to about $3 \times 10^6$ g/mol. The hydroxyl groups of each glucose unit can be substituted with from one to three sulfate groups. The sulfonation imparts water solubility to the otherwise insoluble cellulose. The availability of unsubstituted hydroxyl groups provides reactive sites for crosslinking for the soluble cellulose sulfate. The negative charge of the sulfate group is balanced by the positive charge of a cationic species, typically an alkali metal cation, and preferably the sodium cation. In certain embodiments, the polymer matrix that forms the scaffold can additionally comprise a water soluble cellulose compound, e.g., NaCS.

The term "collagen" can mean, but is not limited to, any of a family of extracellular, closely related proteins occurring as a major component of connective tissue, giving it strength and flexibility. At least fourteen (14) types exist, each composed of tropocollagen units that share a common triple-helical shape but that vary somewhat in composition between types, with the types being localized to different tissues, stages, or functions. In some types, including the most common, Type I, the tropocollagen rods associate to form fibrils or fibers; in other types the rods are not fibrillar but are associated with fibrillar collagens, while in others they form nonfibrillar, non-periodic but structured networks. Tropocollagen, the basic structural unit of collagen comprises a helical structure consisting of three polypeptide chains, each chain composed of about a thousand amino acids, coiled around each other to form a spiral and stabilized by inter- and intrachain covalent bonds. It is rich in glycine, which occurs as nearly one residue out of three, as well as proline, hydroxyproline, and hydroxylysine; the last two rarely occur in other proteins.

The term "microscale fiber" or "micron sized fiber" can mean, but is not limited to, fibers whose diameter ranges from about 1 micrometer ($10^{-6}$ m) to about 1000 micrometers.

The term "nanoscale fiber" or "nano sized fiber" can mean, but is not limited to, fibers whose diameter ranges from about 1 nanometer ($10^{-9}$ m) to about 1000 nanometers.

In certain embodiments, the degradable polymer is selected from the group consisting of a poly(lactic acid-glycolic acid), a poly(lactic acid), a poly(glycolic acid), a poly (orthoester), a poly(phosphazene), poly(or polycaprolactone, a polyamide, a polysaccharide, and a collagen. In a preferred embodiment, the polymer is poly(lactic acid-glycolic acid).

As used herein, the terms "poly(glycolic acid)", polyglycolide, and "PGA" are used interchangeably herein to refer to a biodegradable, thermoplastic polymer and the simplest linear, aliphatic polyester. PGA may be obtained commercially, for example, from Sigma-Aldrich.

A "polylactide" is a biodegradable polymer derived from lactic acid. Poly(lactide) or PLA exists in two stereo forms, signified by a D or L for dexorotary or levorotary, or by DL for the racemic mix. The term "PLLA" refers to the biodegradable aliphatic polyester homopolymer poly L-lactic acid. PLLA may be obtained commercially, for example, from Alkermes, Inc.

The terms poly(lactic acid-glycolic acid), poly(D,L-lactide-c-glycoside), and PLGA are used interchangeably to refer to a copolymer of polylactic acid and glycolic acid. PLGA may be obtained commercially, for example, from Alkermes, Inc.

As used herein, the term "polysaccharide" is a long-chain natural or synthetic polymer made up of linked simple sugars (monosaccharides) such as glucose and closely related molecules. Two monosaccharide molecules may be joined by a glycosidic bond to form a disaccharide, as, for instance, in the linkage of glucose and fructose to create sucrose. More complicated polysaccharides such as starch, glycogen, cellulose or chitin consist of numerous monosaccharide units joined by glycosidic bonds.

As used herein, the term "porous" relates to having one or more openings, pores, perforations or holes that may be filled or perfused by a liquid and/or a gas, or that allows for the flow of a liquid and/or gas therethrough.

The term "growth factor" refers generally to bioactive cell signaling molecules, including cytokines and chemokines, which are known to elicit physiological effects through their interaction with cell surface receptors (typically receptor tyrosine kinases, Ser/Thr kinases, immunoglobulins or GPCRs) on a cell. The phyiological effects of growth factor binding to its receptor include, for example, changes in gene expression, and/or cell proliferation, differentiation, activation, quiescence, or apoptosis. In certain cases, growth factors are pleiotropic, i.e., they may induce different physiological effects depending on the concentration, cell type, and/or cell status. In any of the embodiments provided herein, the fiber, matrix, and/or scaffold may additionally include one or more growth factors to enhance, e.g., cell or tissue growth, differentiation, and/or repair.

The term "bioactive" and "bioactivity" can mean, but is in no way limited to, any effect on, interaction with, or response from living tissue.

As used herein, the term "fluid" can mean, but is in no way limited to, a material and/or a combination of materials capable of flowing. For example, a fluid for use in any of the embodiments described herein may include a liquid component and/or a non-liquid component (e.g., gas, solid, semi-solid, particulate, colloid) such as in a solution, a suspension, a dispersion or a combination thereof. By way of further example, the phrase "cellular isolate fluid" comprises a combination of a liquid component and a cellular or tissue-derived material.

The following embodiments of the present invention will be described in the context of a system, including an apparatus and method, for seeding, culturing, storing, shipping, and testing vascular grafts, although those skilled in the art will recognize that the disclosed methods and structures are readily adaptable for broader application. Note that whenever the same reference numeral is repeated with respect to different figures, it refers to the corresponding structure in each such figure.

II. Exemplary Systems

FIG. 1 illustrates an exemplary closed system 1000 provided by the invention for seeding, culturing, storing, shipping and/or testing cells and/or grafts, e.g., tissue grafts.

In certain embodiments, the system includes a means for containing a cellular isolate, e.g., a cellular isolate fluid. In certain embodiments the means is a container 3 such as a media bag or any flexible or rigid container capable of being sterilized and/or that is hermetically sealed. For example, a Gibco-BFL 1 L media bag could be used. In certain embodiments, cellular isolate fluid container 3 may be composed of any biocompatible, rigid material capable of being sterilized such as Teflon, polycarbonate, PVC, or stainless steel. Container 3 can have any suitable volume for containing the cellular isolate fluid.

In a preferred embodiment, the container 3 has at least one port adapted for the sterile filling and/or dispensing of a fluid, for example, a bone marrow aspirate. For example, a bone marrow aspirate (e.g., 5 cc/kg body weight) is aseptically collected and passed, e.g., injected, into container 3 via port 1 or port 2. In another preferred embodiment, the container 3 has at least one inlet and one outlet. In still another embodiment, the container 3 includes a port having one or more valves to allow for the one-way flow of a fluid or gas. For example, using the embodiment shown in FIG. 1 for reference, port 1 can include and/or take the form of a swabbable valve, such as a needleless access port. The valve can be connected to container 3, and/or can be associated with a fluid line communicating with the container 3, using any suitable coupling or fastening means which is known to those in the art, e.g., a clamp, screw or luer connector, pressure fitting, friction fitting, coupling or the like. In accordance with the embodiment of the system 1000 illustrated in FIG. 1, valve 5 is associated with a conduit, e.g., a fluid line 51, communicating with the container 3. Optionally, the container 3 includes a pre-filter element 4, e.g., comprising, for example, a screen or woven element having openings or a pore structure in the range of, for example, about 40 to about 150 microns. Such pre-filter element could be used to remove undesirable material such as, for example, bone chips, clots, and/or fat deposits, as the fluid passes from the container.

In certain embodiments, the means for containing a cellular isolate fluid comprises a body defining a sterile and/or hermetically sealed container capable of retaining a fluid or gas, wherein the body also defines one or more ports adapted for the filling and/or dispensing of a fluid. In certain embodiments, the body defines one or more ports, wherein at least one port has a valve, e.g., a one-way valve. In still another embodiment, the body defines an outlet port which includes a valve.

Examples of fluid which may be used in the system include, but are not limited to, sterilizing fluid, contrast media fluid, biological fluid, fluid containing cells, blood, serum, bone marrow aspirate, or fluid containing a culture medium. It is to be understood that during testing, seeding, and culturing in a preferred embodiment, the fluid may be advantageously kept at human body temperature, and may be composed of a fluid which approximates the viscosity of human blood. One illustrative example of a solution which approximates the viscosity of blood is saline with glycerol.

The fluid contained in container 3 is passed from the container through fluid line 51 (in FIG. 1). In a preferred embodiment, the fluid is directed away from container 3 by gravity. However, as one of skill in the art would readily appreciate, a fluid pump could also be used (e.g., Masterflex L/S Digital Drive peristaltic pump manufactured by Cole-Palmer, although one skilled in the art could select from a variety of commercially available pumps).

Fluid line 51, as well as all other fluid lines in the system (e.g., lines 52, 53, 54, 55, 56, 57, 58a-58d, and 59), may be made of any type of medical grade, sterilizable, durable tubing suitable for transporting the fluid or gas in use. For example, the fluid line can be flexible or rigid plastic.

The system also includes a flow channel 7 comprising at least one inlet, at least one outlet and at least one filter comprising at least one filter medium (e.g., disposed in a filter housing) therebetween. In a preferred embodiment, the filter is disposed at an angle that is approximately perpendicular to the direction of flow through the flow channel 7 (although in some embodiments, the filter can be disposed at an angle approximately parallel to the direction of flow, e.g., involving tangential flow filtration). In preferred embodiments the filter is adapted to allow flow therethrough in at least two directions, for example, where the first and second directions are approximately opposite, e.g., wherein a fluid can be passed in a first direction from the upstream surface of the filter through the downstream surface, and a fluid can be passed in a second direction from the downstream surface of the filter though the upstream surface. In an example of this embodiment, a cellular isolate fluid is passed in a first direction through a filter having a suitable pore size (or mesh size), wherein the filter medium is at an angle that is approximately perpendicular to the direction of flow such that the filter retains cells and/or biological material that is too large to pass through the filter. A second fluid is subsequently passed in a second direction through the filter which can wash the retained cells and/or biological material off of the filter medium. Filters that can be employed for use in the flow channel are well known in the art and include, for example, Pall Corporation. In still additional embodiments, the filter (e.g., at least one filter medium) has a porosity suitable to retain cells, e.g., bone marrow-derived mononuclear cells. In certain embodiments, the filter comprises a matrix that is designed to reversibly bind and retain the cells of interest based upon, for example, ligand-receptor interactions.

In still additional embodiments, multiple filters can be assembled in series or in parallel for use in the system as described herein.

It is contemplated that the system and method can have any number of desired flowpaths and shutoffs. The liquid or gas can be fed through the system in at least three ways: gravity, such as a IV type bag connected to the filter, positive pressure or negative pressure, such as via a syringe, pump, or vacuum source, all of which are expressly encompassed and contemplated by the present invention.

Connecting to a filter and/or any other component of the system can be done in any number of ways well known in the art, for example, sterile docking, twist on fittings, such as a luer fitting, snap or friction fittings and fasteners, etc. Thus, it would be possible to connect with a variety of standard connection techniques and it is contemplated that any combination of standard connections is possible.

All combinations are encompassed and contemplated by the present invention.

In certain embodiments, the system includes a means for containing a collection fluid. In certain embodiments the means is a container 13, such as a media bag or any flexible or rigid container capable of being sterilized and/or that is hermetically sealed. For example, a Gibco-BFL 1 L media bag could be used. In certain embodiments, collection container 13 may be composed of any biocompatible, rigid material capable of being sterilized such as Teflon, polycarbonate, acrylic, PVC, or stainless steel. Container 13 can have any suitable volume for containing the collection fluid.

In a preferred embodiment, the container 13 has at least one port adapted for the sterile filling and/or dispensing of a fluid, for example, a bone marrow aspirate filtrate or flow through. For example, a bone marrow aspirate (e.g., 5 cc/kg body weight) is aseptically collected and passed, e.g., injected, into container 3 and subsequently passed (e.g., through optional pre-filter 4 and via fluid flow lines 51 and 52) through flow channel 7 including a filter. The filter retains cells and/or the biological material of interest, allowing the filtrate to flow through fluid lines 53 and 54 and inlet port 11 into container 13. In another preferred embodiment, the container 13 has at least one flow port, e.g., a bi-directional flow port; typically, however, the container 13 has at least two ports. In certain embodiments, container 13 comprises an inlet port and/or an outlet port (in the embodiment illustrated in FIG. 1, container 13 comprises an inlet port 11 and an outlet port 14). In still another embodiment, the container 13 includes a port having one or more valves to allow for the one-way flow of a fluid or gas. The valve can be connected to container 13 and/or associated with a fluid line communicating with container 13 using any suitable coupling or fastening means which is known to those in the art, e.g., a clamp, screw or luer connector, pressure fitting, friction fitting, or the like. In accordance with the embodiment illustrated in FIG. 1, the system 1000 includes a valve 10 associated with the fluid line 54.

In certain embodiments, the means for containing the collection fluid comprises a body defining a sterile and/or hermetically sealed container capable of retaining a fluid or gas, wherein the body also defines one or more ports adapted for the filling and/or dispensing of a fluid. In certain embodiments, the body defines one or more ports, wherein at least one port has a valve, e.g., a one-way valve. In still another embodiment, the body defines an outlet port which includes a valve.

In certain embodiments (e.g., after elution fluid is passed through the flow channel 7 and cells are passed into seeding container 18 as noted in more detail below), the collection fluid or filtrate contained in container 13 is passed through fluid lines 59 and 57 into seeding container 18 (in FIG. 1). In a preferred embodiment, the fluid is directed away from container 13 by gravity. However, as one of skill in the art would readily appreciate, a fluid pump could also be used (e.g., Masterflex L/S Digital Drive peristaltic pump manufactured by Cole-Palmer, although one skilled in the art could select from a variety of commercially available pumps). In certain embodiments, the system includes a means for containing an elution fluid. In certain embodiments, the means is a container 9, such as a media bag, syringe, or any flexible or rigid container capable of being sterilized and/or that is hermetically sealed. For example, a Gibco-BFL 1 L media bag could be used. In certain embodiments, elution fluid container 9 may be composed of any biocompatible, rigid material capable of being sterilized such as Teflon, polycarbonate, acrylic, PVC, or stainless steel. Container 9 can have any suitable volume for containing the elution fluid.

In a preferred embodiment, the container 9 has at least one port adapted for the sterile filling and/or dispensing of a fluid, for example, an elution or washing fluid. In certain embodiments, the elution fluid can be a cell culture media, saline, e.g., phosphate buffered saline, saline including dextran, or any other suitable fluid known by those of skill in the art for harvesting or culturing cells, e.g., lactated ringers solution, normal saline, Delbecco's modified Eagles medium, a fluid as disclosed in International Publications WO 98/045413 and WO 05/094914, etc. In another preferred embodiment, the container 9 has at least one flow port, e.g., a bi-directional flow port. In certain embodiments, container 9 comprises an inlet and/or an outlet. In still another embodiment, the container 9 includes a port having one or more valves to allow for the one-way flow of a fluid or gas, and/or one or more valves is associated with a fluid line communicating with the container 9. In accordance with the embodiment illustrated in FIG. 1, the system 1000 includes a valve 8 associated with the fluid line 55. The valve can be connected to container 9 and/or associated with the fluid line using any suitable coupling or fastening means which is known to those in the art, e.g., a clamp, screw or Luer connector, pressure fitting, friction fitting, or the like. The elution or wash fluid is passed through valve 8 and fluid line 53, flow channel 7, fluid lines 52, 56, and 57, into seeding container 18 (in FIG. 1).

In certain embodiments, the means for containing the elution or wash fluid comprises a body defining a sterile and/or hermetically sealed container capable of retaining a fluid or gas, wherein the body also defines one or more ports adapted for the filling and/or dispensing of a fluid. In certain embodiments, the body defines one or more ports, wherein at least one port has a valve, e.g., a one-way valve. In still another embodiment, the body defines an outlet port which includes a valve.

In one embodiment, container 9 is a syringe filled with a sterile elution or wash fluid. The elution or wash fluid is passed through flow channel 7 and into seeding container 18 through valve 8, fluid lines 53, 52, 56 and 57 (in FIG. 1). In this embodiment, the fluid is directed away from container 9 due to pressure exerted on the fluid by depressing the syringe plunger, for example, manually or via a mechanical and/or electrical device. Alternatively, for example, the container 9 can be a flexible container that can be compressed. However, as one of skill in the art would readily appreciate, a fluid pump could also be used (e.g., Masterflex L/S Digital Drive peristaltic pump manufactured by Cole-Palmer, although one skilled in the art could select from a variety of commercially available pumps).

In certain embodiments, the system includes a means for containing a cell seeding assembly. In certain embodiments, the means is a seeding container 18, such as a media bag or any flexible or rigid container capable of being sterilized and/or that is hermetically sealed. For example, a Gibco-BFL 1 L media bag could be used. In certain embodiments, container 18 may be composed of any biocompatible, rigid material capable of being sterilized such as Teflon, polycarbonate, acrylic, PVC, or stainless steel. Seeding container 18 can have any suitable volume.

In certain embodiments, seeding container 18 may be comprised of two or more sections which are secured and made leak proof through any standard means, such as inner and outer threads or the use of bonding agents. For example, in accordance with the embodiment illustrated in FIG. 1, the seeding container 18 comprises a rigid material comprising a main body section including threads, and a threaded cap 17. Alternatively, in accordance with the embodiment of the seeding container 18 shown in FIG. 1A, the seeding container comprises a flexible material such as a bag. In order to view the scaffold or graft, e.g., vascular graft, within container 18, a viewing port may be placed at any point or location on the container, or alternatively, the container may be made of an optically clear material such as polycarbonate or PVC.

In a preferred embodiment, the seeding container 18 has at least one port adapted for the sterile filling and/or dispensing of a fluid, for example, an elution or wash fluid and/or collection or filtrate fluid as described herein. In certain embodiments, container 18 comprises an inlet and/or an outlet. In still another embodiment, the container 18 comprises at least an inlet and an outlet port (in the embodiments illustrated in FIG. 1 and FIG. 3, seeding container 18 comprises an inlet port 16, an outlet port 24, a sampling port 19 (e.g., for aseptic acquisition of fluid samples from the seeding container to determine, for example, microbial contamination and/or stem cell enumeration), and a vent port 26, wherein the cap 17 (FIG. 1 only) comprises the ports). Using the embodiments shown in FIG. 1 and FIG. 3 for reference, port 19 can include a swabbable valve, such as a needleless access port. In a particularly preferred embodiment, the outlet port is adapted with a cell seeding assembly 100 (see FIG. 3). In certain embodiments, the container 18 comprises an inlet port having one or more valves to allow for the one-way flow of a fluid or gas. Alternatively, or additionally, one or more valves can be associated with one or more fluid lines communicating with the seeding container. The valve can be connected to container 18 and/or associated with a fluid line communicating with seeding container 18 using any suitable coupling or fastening means which is known to those in the art, e.g., a clamp, screw or luer connector, pressure fitting, friction fitting, or the like.

In a preferred embodiment, seeding container 18 comprises an inlet port 16 and outlet port 24, which allows for the perfusion and/or circulation of fluid into and through the container. Inlet port 16 and outlet port 24 are also used to attach container 18 to fluid lines 57 and 58a, respectively. Fluid line 58a connects seeding container 18 to one or more residual seeded cell fluid containers 35a and 35b, while maintaining a closed system. It is to be understood that although only one seeding container 18 is shown in FIG. 1, a fluid line, e.g., fluid line 57 or 58a, may be branched so as to connect more than one seeding container in parallel to the system.

Optionally, the seeding container 18 can further comprise at least one vent, e.g., comprising at least one hydrophobic microporous membrane (preferably, disposed in a housing) as disclosed in, for example, International Publication WO 91/017809. For example, in the embodiments illustrated in FIG. 1 and FIG. 3, a vent 26, preferably, providing a bacterial blocking pore rating, can be placed in communication with at least one seeding container port 25. Without being bound to any particular theory or mechanism, the vent may allow for gas exchange, e.g., while the seeded scaffold is bathed.

In certain embodiments, the means for containing the seeding assembly comprises a body defining a sterile and/or hermetically sealed container capable of retaining a fluid or gas, wherein the body also defines one or more ports adapted for the filling and/or dispensing of a fluid, and a seeding assembly. In certain embodiments, the body defines one or more ports, wherein at least one port has a valve, e.g., a one-way valve. In still another embodiment, the body defines an outlet port.

In certain embodiments, the means for containing residual seeded cell fluid is at least one residual seeded cell fluid container 35a, 35b, such as a media bag or any flexible or rigid container capable of being sterilized and/or that is hermetically sealed. For example, a Gibco-BFL 1 L media bag could be used. In certain embodiments, containers 35a, 35b may be composed of any biocompatible, rigid material capable of being sterilized, such as Teflon, polycarbonate, PVC, or stainless steel.

In a preferred embodiment, fluid is drawn out of container 18 into a residual seeded cell fluid container 35a via port 25 and fluid line 58a through the use of vacuum assembly comprising a vacuum source, e.g., a pump, and a regulator 28, wherein the negative pressure from the pump is conveyed through fluid lines connected to residual seeded cell fluid container 35a, 35b and seeding container 18.

In certain embodiments, seeding container 18 houses a seeding assembly 100 comprising a porous tube 20 and a scaffold 21, e.g., cell or tissue scaffold or graft, such as a vascular graft scaffolding. The porous tube 20 may be comprised of any suitable rigid material, such as Teflon, PVC, polycarbonate, plastic, metal, e.g., stainless steel, which may be made fluid permeable. One illustrative example of a suitable porous tubing is the porous plastic tubing manufactured by Porex Technologies. Alternatively, porous tube 20 may be comprised of any suitable elastomeric material, such as PET or angioplasty balloons, that is capable of expanding and contracting, and that may be made fluid permeable. Seeding container 18 and tube 20 may both be made any length or diameter so as to hold vascular graft scaffolding 21 of any length or diameter. This is advantageous, as the system may be used to sterilize, seed, culture, store, ship, and test vascular grafts of any size. One or more retaining elements such as clips, o-rings, or grommets may also be placed on tube 20, e.g., at both ends of scaffolding 21, to hold the scaffolding in place on the tube during seeding, culturing, storing, shipping, or treatment.

Figure 2:
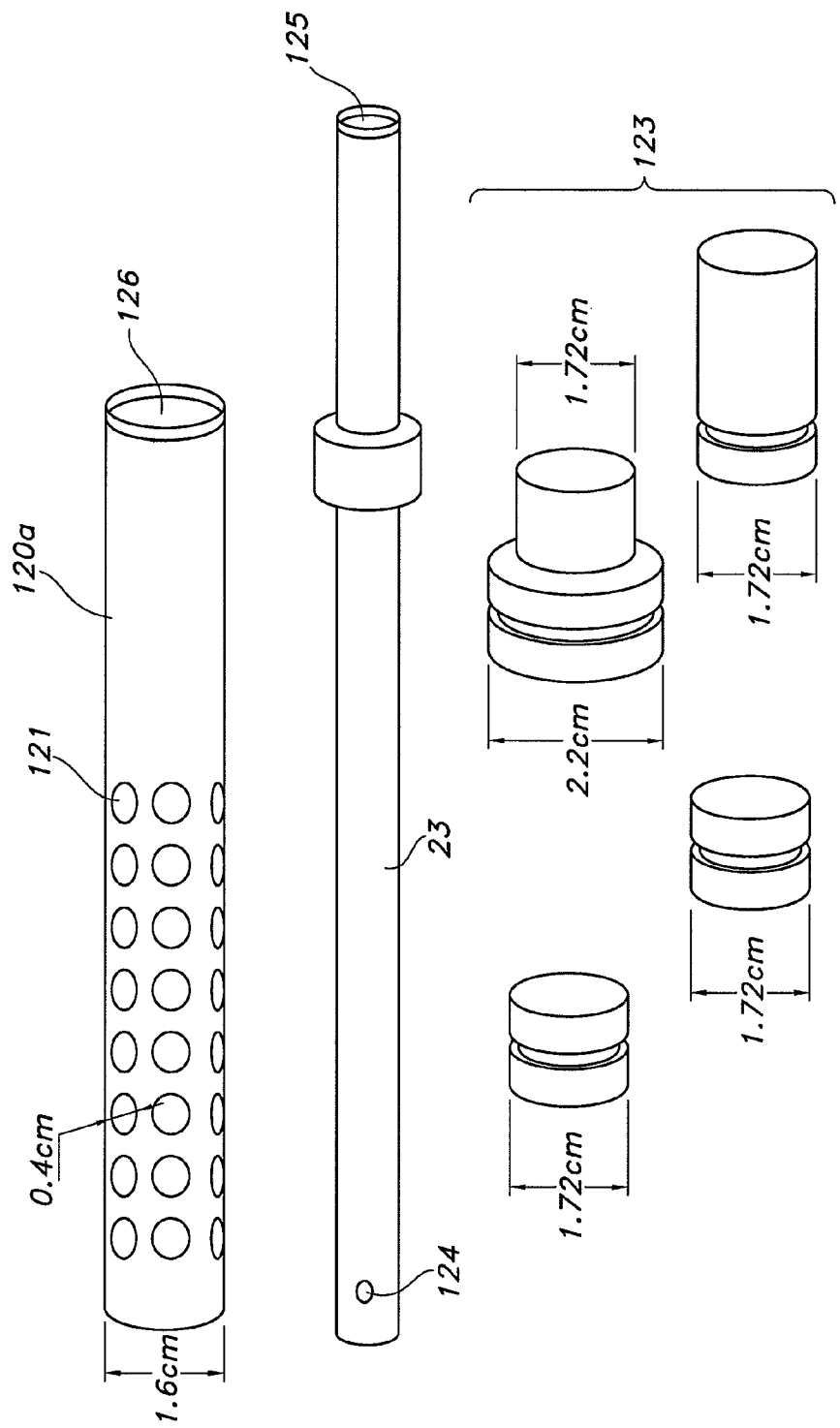
FIG. 2 demonstrates an exemplary mandril design for use with an exemplary system as described herein. Briefly, (i) the open end (126) of the perforated mandril (20) is inserted over the suction rod (23); (ii) the appropriate sized coupling rings (123) are then inserted over the perforated mandril; and (iii) the appropriate sized scaffold is then inserted over the apparatus and secured.

In certain embodiments, the porous tube 20 comprises a mandril 120a. An exemplary mandril is illustrated in FIG. 2. With reference to FIG. 2: the open end 126 of the mandril manifold 120 is inserted over the suction rod 23 having an aperture 124 near the closed end of the suction rod. The mandril is then affixed, e.g., with appropriate sized coupling rings 123, which are then inserted over the perforated mandril, and, illustratively, the mandril 120a is frictionally held in the seeding container 18 via one or more o-rings 22 (shown in FIG. 1). This assembly allows for the movement of fluid through the mandril manifold 120 into the aperture 124 and out opening 125. As described herein, fluid is directed out of the seeding container 18 via suction rod 23 through the mandril via a vacuum means (for example a pump) communicating with residual seeded cell fluid containers 35a, 35b, and to the mandril 120a through fluid lines 58a-58d.

In a preferred embodiment, the mandril 120a comprises a plurality of holes or perforations 121. However, it should be understood that the perforations may be of any desired size, shape, and/or configuration, which can be varied in any number of ways that would be obvious to the skilled artisan in view of the present description, and are encompassed and contemplated by the present invention. It is also contemplated that the porous tube 20 can be of any desired length and/or diameter. For example, the diameter may be varied to account for different graft sizes and/or applications, which are expressly encompassed and contemplated by the present invention.

In certain embodiments, the seeding container 18 houses a seeding assembly 100 comprising a porous tube 18 and a scaffold 21. The scaffold can be naturally derived, e.g., placental tissue, or synthesized. For example, synthetic cell and/or tissue scaffolds are known in the art and are commercially available. One suitable example of a scaffold is disclosed in International Publication WO 09/019,995. In certain embodiments, the scaffold to be used can be a three-dimensional matrix formed of polymeric (homopolymer and/or copolymer) fibers that are assembled in a woven or non-woven mesh, in random or aligned configurations. In a preferred embodiment, the fiber matrix of the scaffold comprises pores of a suitable size to allow cells to adhere and grow and/or differentiate. Since the diameter of a cell is approximately 10 µm to 20 µm, pore sizes within this range are desired in certain embodiments. In addition, the polymeric scaffolds provided by the invention can be generated or fabricated in order to more closely mimic the structure and composition of the natural extracellular matrix in order to promote growth and differentiation of the seeded cell and to facilitate transplantation and/or implantation of the scaffold or cells grown on the same. The fibers comprising the scaffold matrix can be of any desired size, but generally are between about 1.5 mm and 1 nm. In certain embodiments, the fibers are nanoscale (i.e., from about 1 nm to about 1000 nm) and/or microscale (from about 1 µm to about 1000 µm). In certain embodiments, the scaffolds of the invention additionally comprise one or more growth factors capable of facilitating cell growth and/or differentiation.

Polymers useful for creating a scaffold for use in the present invention may be inorganic (e.g., siloxane, sulfur chains, black phosphorus, boron-nitrogen, silicones) or organic (meaning containing carbon). Organic polymers may be natural [e.g., polysaccharides, such as starch, cellulose, pectin, seaweed gums, vegetable gums; polypeptides, such as casein, albumin, globulin, keratin, collagen, insulin, DNA; and hydrocarbons], synthetic [such as thermoplastics (unvulcanized elastomers, nylon, polyvinyl chloride, linear polyethylene, polystyrene, polypropylene, polyurethane, acrylate resins); thermosetting (e.g., vulcanized elastomers, crosslinked polyethylene, phenolics, alkyds, polyesters), and semisynthetic (e.g., cellulosics, such as rayon, methylcellulose, cellulose acetate; and modified starches)]. In addition, scaffolds useful in the present invention may comprise hydrogels formed from water soluble or water insoluble cellulose compounds. As would be readily understood by the skilled artisan, the particular type and composition of scaffold will vary depending upon the desired application. However, it is generally preferred that the polymeric material comprising the scaffold be biocompatible (i.e., will not elicit an unwanted immune reaction).

In certain embodiments, the scaffold is biodegradable. In any embodiment, the degradable polymer is selected from the group consisting of a poly(lactic acid-glycolic acid), a poly (lactic acid), a poly(glycolic acid), a poly(orthoester), a poly (phosphazene), poly(or polycaprolactone, a polyamide, a polysaccharide, and a collagen. In a preferred embodiment, the polymer is poly(lactic acid-glycolic acid).

In any of the embodiments described herein, the scaffold can be apposed to the porous tube, e.g., a mandril as described herein, in the seeding assembly. For example, it is contemplated that the scaffold may be in contact with only a portion of the porous tube. Alternatively, it is contemplated that the scaffold may substantially surround some or all of the porous tube. In general, it is preferred that the scaffold be in juxtaposition or adjacent to the perforated portion of the porous tube such that fluid flows through as much of the scaffold as possible to facilitate seeding of as many cells as possible.

In accordance with embodiments of the invention, a plurality of seeding containers, e.g., comprising seeding assemblies comprising porous tubes (preferably, mandrils and scaffolds) can be pre-assembled, e.g., for different size grafts and/or different applications, and assembled as part of the system when desired. Typically, for example, the seeding containers are pre-assembled and sterilized, and can be sterilely connected to the rest of the system, e.g., by sterile docking. Thus, the optimal system can be quickly set up when needed.

In another preferred embodiment, the flow channel is positioned between the cellular isolate container, collection fluid container, elution or wash fluid container, and the seeding container. This configuration is exemplified by FIG. 1. In still another embodiment, the flow channel is selectively in fluid communication with each of the same. In an embodiment, a housing comprises the flow channel, including an inlet, outlet, and a filter comprising at least one filter medium, e.g., a porous leukocyte depletion medium (for example, in a preferred embodiment, the flow channel comprises filter device comprising a housing having an inlet and an outlet and defining a fluid flow path between the inlet and an outlet, and a filter comprising at least one porous filter medium disposed in the housing across the fluid flow path). In another embodiment the housing comprises the flow channel, inlet, outlet, and filter therebetween, and a valve. In certain embodiments, the valve has at least one open position and at least one closed position.

In any of the preferred embodiments, the system provided by the invention comprises flow lines that permit the flow of a fluid and/or gas therethrough.

Accordingly, in a preferred embodiment, the invention provides a system for the seeding, culture, storage, shipping, and/or testing of a cell or tissue graft comprising a cellular isolate fluid container; a flow channel disposed between the cellular isolate fluid container, a collection fluid container, an elution fluid container, and a seeding container, wherein the flow channel comprises an inlet, an outlet and a filter therebetween, wherein the filter is adapted to allow flow in at least two directions, and wherein the flow channel is selectively in fluid communication with each of the cellular isolate fluid container; the collection fluid container, the elution fluid container, and the seeding container, respectively; and wherein the seeding container comprises a seeding assembly.

In one embodiment, the seeding assembly comprises a perforated mandril, and a biocompatible three-dimensional scaffold which is apposed to at least a portion of the mandril.

In still another embodiment, the system comprises at least one residual seeded cell fluid container, wherein the residual seeded cell fluid container is selectively in fluid communication with the seeding container.

In another embodiment, the system comprises a vacuum source in fluid communication with the residual seeded cell fluid container.

The exemplary embodiments of system as described herein (see FIGS. 1, 2 and 3) allow for the isolation of bone marrow-derived mononuclear cells, and, while maintaining an aseptic system, or while maintaining a closed sterile system, seeding the cells onto a biocompatible three-dimensional scaffold, which after a brief period of incubation (e.g., about three (3) hours or less, more preferably, about two (2) hours or less) can be used as a tissue engineered vascular graft.

As would be recognized by one of skill in the art, in accordance with embodiments of the invention, the system can be used while maintaining an aseptic system, wherein a sterile seeding container can be assembled (e.g., with the desired porous tube and scaffold) using aseptic techniques, in a sterile field, such as the operating room, using sterile gloves to handle the components. The assembled seeding container can be connected to the other components of the system, e.g., wherein the cell isolation container, elution container, and collection container have already been pre-assembled in a closed sterile manner.

Alternatively, and preferably, the system can be used while maintaining a closed sterile system, wherein the system has been pre-assembled and sterilized before use.

In certain embodiments, the system is disposable. The closed disposable system allows for a procedure for the construction of tissue engineered graft, e.g., a vascular graft, that can be performed rapidly while achieving similar seeding efficiency as compared to previously described methods. See, e.g., Matsumura G, Hibino N, Ikada Y, Kurosawa H, Shinoka T. Successful application of tissue engineered vascular autografts: clinical experience. Biomaterials 2003; 24:2303-8; and FDA IDE 14127, which are incorporated herein by reference in their entirety. In addition, the use of the system as described herein offers the opportunity to construct the tissue engineered graft, e.g., vascular graft, at the point of care (i.e., in the operating room precluding the need for scaffold transport.

The aseptic or closed system for seeding cells onto a three dimensional scaffold as described herein combines filter cell isolation, vacuum seeding, and container (e.g., bag) technology for use in tissue engineering in a way not previously described. Advantages of this technology include that it enables the assembly of a tissue engineered construct without the need for sterile hood or ISO Class 7 room dramatically reducing the cost for producing tissue engineered products while simultaneously increasing the clinical utility of the use of the tissue engineered product by precluding the need for such equipment or facilities. Another advantage is that it provides a graft in less time that previously available.

III. Exemplary Methods

Tissue engineered vascular graft with bone marrow derived mononuclear cells may be obtained according to exemplary methods of the present disclosure.

With reference to FIG. 1, in an additional aspect, the invention provides methods for seeding cells onto a scaffold comprising, for example, providing the cell seeding system according to any of the methods described herein, wherein at least one valve is disposed between the flow channel and each of the cellular isolate fluid container, collection fluid container, elution fluid container, and the seeding container, respectively, and wherein a first phase is defined by the flow channel being in fluid communication only with the cellular isolate fluid container and the collection fluid container; directing flow of fluid in a first direction from the cellular isolate fluid container to the collection fluid container, wherein the cells from the cellular isolate fluid are retained on the filter; closing at least one valve such that the flow channel is not in fluid communication with the collection fluid container or the cellular isolate fluid container, wherein a second phase is defined by the flow channel being in fluid communication only with the elution fluid container and the seeding container; directing flow of the elution solution from the elution fluid container through the flow channel filter in a direction approximately opposite from the first direction, such that the cells are substantially removed from the filter and flow into the seeding container; and removing the fluid from the seeding container by directing flow through the biocompatible three-dimensional scaffold and the perforated mandril into the residual seeded cell fluid container, whereby at least a portion of the cells in the seeding container are seeded onto the scaffold.

In one embodiment, the fluid is removed from the seeding container by a vacuum, e.g., −20 mm Hg (or another suitable value less than the bubble point of the filter in the flow channel 2), which is applied until all of the cell suspension has passed through the scaffold and is collected in the residual seeded cell fluid containers 35*a*, 35*b*.

In another embodiment, a housing comprises the flow channel, including an inlet, outlet, and filter. In another embodiment the housing comprises the flow channel, inlet, outlet, and filter therebetween, and a valve. In certain embodiments, the valve has at least one open position and at least one closed position.

Figure 1A:
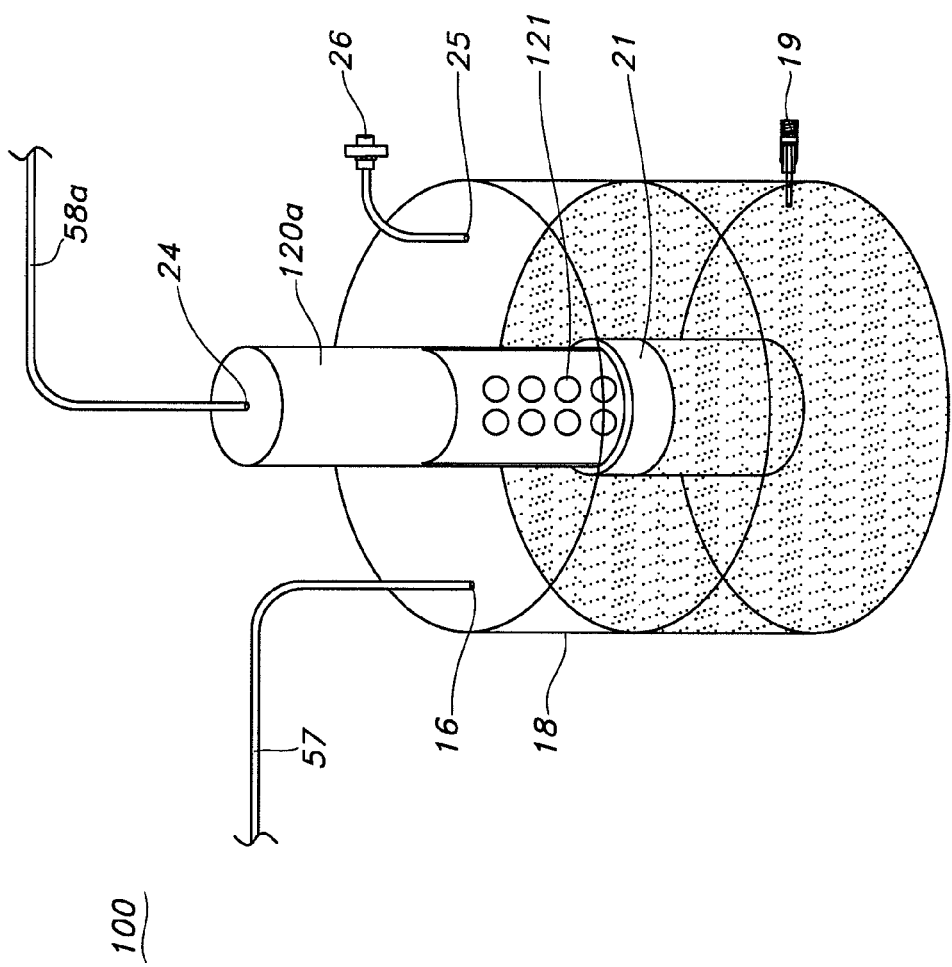
FIG. 1A is a perspective view of the seeding container (18) shown in FIG. 1, illustrating cell suspension in the seeding container, wherein the suspension contacts the scaffold.

Accordingly, in another embodiment, and using the illustrative system 1000 shown in FIG. 1 (wherein the seeding assembly 18 shown in FIG. 3 can also be used in the system) for general reference, the method comprises collecting a bone marrow aspirate (e.g., 5 cc/kg body weight), aseptically, into container 3, wherein at least valve 51 is closed (typically, one or more of valves, 6, 7, 8, 10, and 15 are also closed). Clamps 5 and 10 are opened, and, using gravity, the bone marrow aspirate is passed (via fluid lines 51 and 52) through the flow channel 7 filter, which traps the bone marrow derived-mononuclear cells. The remaining portion of the bone marrow aspirate (typically, composed primarily of plasma) is collected (via fluid lines 53 and 54 and port 11) in collection fluid container 13. Subsequently, clamps 5 and 10 are closed, valves 8 and 6 are opened, and the elution solution is passed (via fluid lines 55 and 53) through the filter 7 releasing the bone marrow-derived mononuclear cells which pass through fluid lines 52, 56, and 57 and port 16 and are collected in the seeding container 18. The seeding container 18 contains the seeding assembly 100, including the scaffold 21 that is inserted over a perforated porous tube 20/mandril 120*a*. In a preferred embodiment, the bone marrow-derived mononuclear cell suspension fills the seeding container 18 completely covering the scaffold 21 that is inserted over the perforated mandril 20 (FIG. 1A shows the cell suspension in contact with the scaffold). Subsequently, valves 6 and 10 are closed, and valve 27 is opened, and a vacuum (e.g., −20 mm Hg) using a vacuum assembly including a regulator 28, is applied until all of the cell suspension has passed through the scaffold and is collected, via port 24 and fluid line 58*a* in residual seeded cell fluid container 35*a* (if there is excess fluid, the additional cell suspension is collected, via fluid line 58*b*, in residual seeded cell container 35*b*).

After vacuum has ceased, valve 27 is preferably closed, valve 15 is opened, and the serum in container 13 is allowed to drain by gravity via fluid lines 59 and 57 and port 16 into seeding container 18 thus bathing the seeded scaffold. If the optional vent 26 is included as part of the seeding container 18, gas exchange may occur, e.g., during bathing. If desired, e.g., for ease of handling the seeding container and/or the seeding container components (such as the mandril and/or scaffold) while the cells are being bathed, one or more system components upstream of the seeding container 18, such as filter 7, elution container 9, collection container 13, and/or the cellular isolate container 3 can be removed (e.g., after heat sealing the appropriate fluid line) and discarded. As an additional option, the entire apparatus is placed in an incubator at, e.g., approximately 10-100% humidity, 35-37° C., with 3-5% $CO_2$) for approximately two hours after which the seeded scaffold can be aseptically removed from the container (e.g., after removing the cap 17 (FIG. 1) or after cutting open the flexible container (FIG. 3)) and used as a tissue engineered vascular graft.

IV. Exemplary Kits

In an additional aspect, the invention provides kits comprising at least one container comprising a system or apparatus according to any of the embodiments described herein and directions for its use.

V. EXAMPLES

It should be appreciated that the exemplary embodiments of the present invention should not be construed to be limited to the examples that are described herein; rather, the exemplary embodiments of the present invention should be construed to include any and all applications provided herein and all variations within the skill of the ordinary artisan.

VI. Incorporation by Reference

The contents of all references, patents, pending patent applications, published patent applications and published patents, cited throughout this application are hereby expressly incorporated by reference.

VII. Equivalents

Those skilled in the art will recognize, or be able to ascertain using no more than routine experimentation, many equivalents to the specific embodiments of the invention described herein. Such equivalents are intended to be encompassed by the following claims.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A system for seeding cells comprising:
    a cellular isolate fluid container;
    a flow channel disposed between the cellular isolate fluid container, a collection fluid container, an elution fluid container, and a seeding container, wherein the flow channel comprises an inlet, an outlet and a filter therebetween;
    at least one residual seeded cell fluid container, wherein the residual seeded cell fluid container is selectively in fluid communication with the seeding container; and
    a vacuum source in fluid communication with the residual seeded cell fluid container and a suction rod having a closed end, an open end, and an aperture; wherein
    the filter is adapted to allow flow in at least two directions;
    the flow channel is selectively in fluid communication with each of the cellular isolate fluid container, the collection fluid container, the elution fluid container, and the seeding container, respectively;
    the seeding container comprises a vent, a cell seeding assembly, and a perforated mandril having an open end, wherein the suction rod is positioned within the mandril; and
    the system is a closed system.

2. The system of claim 1, wherein a housing comprises the flow channel, inlet, outlet, and filter therebetween.

3. The system of claim 1, wherein the seeding container comprises a threaded body and a threaded cap.

4. The system of claim 1, wherein the seeding container comprises a flexible bag.

5. The system of claim 1, wherein the seeding container comprises a biocompatible three-dimensional scaffold which is apposed to at least a portion of the mandril.

6. The system of claim 5, wherein the biocompatible three-dimensional scaffold is biodegradable.

7. The system of claim 6, wherein the biocompatible three-dimensional scaffold comprises a matrix of polymer fibers.

8. The system of claim 7, wherein the fibers comprise at least one polymer selected from the group consisting of a poly(lactic acid-glycolic acid), a poly(lactic acid), a poly(glycolic acid), a poly(orthoester), a poly(phosphazene), polycaprolactone, a polyamide, a polyvinyl polymer or co-polymer, a polysaccharide, a collagen, and combinations thereof.

9. The system of claim 8, wherein the fibers comprise poly-l-(lactide acid).

10. The system of claim 1, wherein the system comprises a plurality of seeding containers.

11. The system of claim 10, wherein the plurality of seeding containers is selectively in fluid communication with a manifold, which is selectively in fluid communication with the flow channel, and comprises an inlet, a valve, and a plurality of outlets, and wherein the manifold is adapted to distribute fluid and/or gas substantially equally to each seeding container.

12. The system of claim 5, wherein the scaffold is a tissue graft capable of facilitating three dimensional tissue growth on the graft.

13. The system of claim 12, wherein the tissue graft is an implantable vascular tissue graft.

14. The system of claim 13, wherein the vascular tissue graft surrounds at least a portion of the mandril.

15. The system of claim 1, wherein the cellular isolate fluid is sterile.

16. The system of claim 1, wherein the elution solution is sterile.

17. The system of claim 1, wherein each of the cellular isolate fluid container, elution fluid container, collection fluid container, seeding container, and residual cell fluid container comprises an inlet and an outlet.

18. A method for seeding cells onto a scaffold comprising:
providing the system of claim 1, wherein at least one valve is disposed between the flow channel and each of the cellular isolate fluid container, collection fluid container, elution fluid container, and the seeding container, respectively, and wherein a first phase is defined by the flow channel being in fluid communication only with the cellular isolate fluid container and the collection fluid container;
directing flow of fluid in a first direction from the cellular isolate fluid container to the collection fluid container, wherein the cells from the cellular isolate fluid are retained on the filter;
closing at least one valve such that the flow channel is not in fluid communication with the collection fluid container or the cellular isolate fluid container, wherein a second phase is defined by the flow channel being in fluid communication only with the elution fluid container and the seeding container;
directing flow of the elution solution from the elution fluid container through the flow channel filter in a direction approximately opposite from the first direction, such that the cells are substantially removed from the filter and flow into the seeding container; and
removing the fluid from the seeding container by directing flow through the biocompatible three-dimensional scaffold and the perforated mandril into the residual cell fluid container, whereby at least a portion of the cells in the seeding container are seeded onto the scaffold.

19. The method of claim 18, wherein the method includes, prior to
removing the fluid in the seeding container:
closing a valve between the flow channel and the elution fluid container, wherein a third phase is defined by the collection fluid container being in fluid communication only with the flow channel and/or the seeding container; and
directing flow of fluid from the collection fluid container to the seeding container.

20. The method of claim 19, wherein the flow of fluid in at least one of the first phase, second phase, or third phase is due to gravity.

21. The method of claim 18, wherein the fluid is removed from the seeding container by a vacuum.

22. The method of claim 18, wherein a housing comprises the flow channel, inlet, outlet, and filter therebetween.

23. A closed system for culturing cells, comprising:
a first means for containing a cellular isolate;
a second means for directing fluid flow disposed between the first means,
a third means for collecting fluid,
a fourth means for containing an elution fluid,
a fifth means for containing a cell seeding assembly, wherein the second means comprises a filter,
a sixth means for directing fluid flow,
wherein the filter is adapted to allow flow in at least two directions, wherein the second means is selectively in fluid communication with each of the first means, third means, fourth means, and fifth means, respectively, and wherein a biodegradable, biocompatible three-dimensional scaffold is apposed to at least a portion of the sixth means;
a seventh means for containing residual seeded cell fluid which is in fluid communication with the fifth means; and
an eighth means for removing residual seeded cell fluid which is in fluid communication with the seventh means and a suction rod having a closed end, an open end, and an aperture, wherein each of the first means, second means, third means, fourth means, fifth means, sixth means, seventh means, and eighth means are connected by a ninth means for facilitating fluid flow,
wherein the sixth means is a perforated mandril having an open end and disposed between the fifth and seventh means, wherein the suction rod is positioned within the mandril.

24. The closed system of claim 23, wherein at least one of the first means, third means, fourth means, fifth means, seventh means, eighth means or combination thereof is a flexible or rigid plastic container.

25. The closed system of claim 23, wherein the ninth means comprises a flexible or rigid fluid line, and at least one valve that permits the selective flow of a medium therethrough.

26. A closed system for culturing cells, comprising:
a first means for containing a cellular isolate;
a second means for directing fluid flow disposed between the first means,
a third means for collecting fluid,
a fourth means for containing an elution fluid,
a fifth means for containing a cell seeding assembly, wherein the second means comprises a filter,
a sixth means for directing fluid flow,
wherein the filter is adapted to allow flow in at least two directions, wherein the second means is selectively in fluid communication with each of the first means, third means, fourth means, and fifth means, respectively, and wherein a biocompatible three-dimensional scaffold is apposed to at least a portion of the sixth means;
a seventh means for containing residual seeded cell fluid which is in fluid communication with the fifth means; and
an eighth means for removing residual seeded cell fluid which is in fluid communication with the seventh means and a suction rod having a closed end, an open end, and an aperture, wherein each of the first means, second means, third means, fourth means, fifth means, sixth means, seventh means, and eighth means are connected by a ninth means for facilitating fluid flow,
wherein the sixth means is a perforated mandril having an open end and disposed between the fifth and seventh means, the biocompatible three-dimensional scaffold comprises a matrix of polymer fibers, the ninth means comprises a flexible or rigid fluid line and at least one valve that permits the selective flow of a medium therethrough, and the suction rod is positioned within the mandril.

27. The closed system of claim 26, wherein the fibers comprise at least one polymer selected from the group consisting of a poly(lactic acid-glycolic acid), a poly(lactic acid), a poly(glycolic acid), a poly(orthoester), a poly(phosphazene), polycaprolactone, a polyamide, a polyvinyl polymer or co-polymer, a polysaccharide, a collagen, and combinations thereof.

28. The closed system of claim 27, wherein the fibers comprise poly-l-(lactide acid).

29. The closed system of claim 25, wherein the biocompatible three-dimensional scaffold comprises a matrix of polymer fibers.

30. The closed system of claim 29, wherein the fibers comprise at least one polymer selected from the group consisting of a poly(lactic acid-glycolic acid), a poly(lactic acid), a poly(glycolic acid), a poly(orthoester), a poly(phosphazene), polycaprolactone, a polyamide, a polyvinyl polymer or co-polymer, a polysaccharide, a collagen, and combinations thereof.

31. The closed system of claim 30, wherein the fibers comprise poly-l-(lactide acid).

32. The closed system of claim 26, wherein at least one of the first means, third means, fourth means, fifth means, seventh means, eighth means or combination thereof is a flexible or rigid plastic container.

33. The closed system of claim 26, wherein the biocompatible three-dimensional scaffold is biodegradable.

34. The system of claim 1, wherein the system provides isolated cells that are seeded onto a biocompatible, three-dimensional scaffold while maintaining a closed, sterile system, wherein the cells can be used as a tissue engineered vascular graft after two hours.

* * * * *